United States Patent [19]

Archibald et al.

[11] Patent Number: 4,673,389
[45] Date of Patent: Jun. 16, 1987

[54] SEQUENCE VALVE FOR PIGGYBACK IV ADMINISTRATION

[75] Inventors: G. Kent Archibald, White Bear Lake; Frank A. Slaker, New Brighton, both of Minn.

[73] Assignee: Minnesota Mining and Manufacturing Company, St. Paul, Minn.

[21] Appl. No.: 676,020

[22] Filed: Nov. 29, 1984

[51] Int. Cl.$^4$ .................. A61M 5/14; F16L 55/14
[52] U.S. Cl. ................................. 604/81; 604/67; 604/250; 251/9
[58] Field of Search ................. 604/80–86.7, 604/7, 28–31, 34, 65–67, 245–250; 128/DIG. 12, DIG. 13; 251/4, 6, 7, 9, 67, 68, 74; 137/636.1

[56] References Cited

U.S. PATENT DOCUMENTS

| | | | |
|---|---|---|---|
| 2,591,216 | 4/1952 | Thompson et al. | 251/68 |
| 3,016,915 | 1/1962 | Moeller, Jr. | 251/6 |
| 3,575,161 | 4/1971 | London | 604/250 |
| 3,895,649 | 7/1975 | Ellis | 251/9 |
| 3,960,224 | 6/1976 | Silvers | 604/250 |
| 4,061,142 | 12/1977 | Tuttle | 604/34 |
| 4,094,318 | 6/1978 | Burke et al. | 604/65 |
| 4,210,138 | 7/1980 | Jess et al. | 128/DIG. 13 |
| 4,230,151 | 10/1980 | Jonsson | 251/7 |
| 4,261,388 | 4/1981 | Shelton | 604/65 |
| 4,373,525 | 2/1983 | Kobayashi | 128/DIG. 13 |
| 4,397,642 | 8/1983 | Lamadrid | 604/65 |
| 4,443,216 | 4/1984 | Chappell | 128/DIG. 12 |
| 4,451,255 | 5/1984 | Bujan et al. | 604/157 |
| 4,460,358 | 7/1984 | Somerville et al. | 604/34 |
| 4,484,591 | 11/1984 | Hanover et al. | 251/4 |
| 4,496,133 | 1/1985 | Sule | 251/7 |
| 4,524,802 | 6/1985 | Lawrence et al. | 604/34 |
| 4,533,347 | 8/1985 | Deckert | 604/250 |
| 4,559,036 | 12/1985 | Wunsch | 604/81 |

FOREIGN PATENT DOCUMENTS 1130107  1/1957  France ..................... 251/9

Primary Examiner—Dalton L. Truluck
Assistant Examiner—Mario Costantino
Attorney, Agent, or Firm—Kinney & Lange

[57] ABSTRACT

A piggyback IV administration system uses a solenoid actuated sequence valve to control the flow of fluid from a pair of IV fluid sources to the inlet of an IV pump or controller. The sequence valve pinches off a first tube while allowing fluid to flow through the second tube and then, in response to a control signal, changes state so that the second tube is pinched off and fluid can flow through the first tube unimpeded.

29 Claims, 12 Drawing Figures

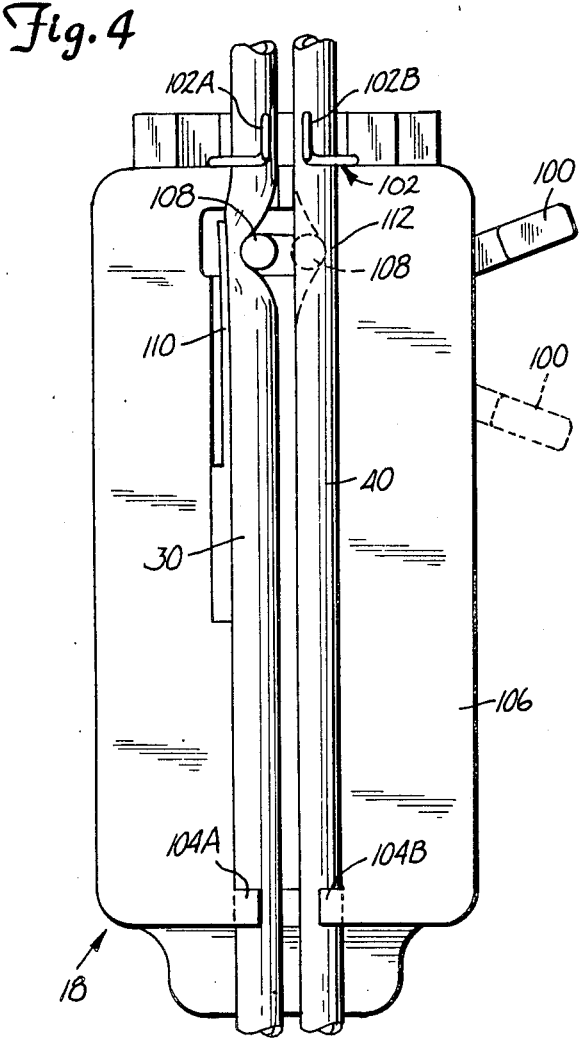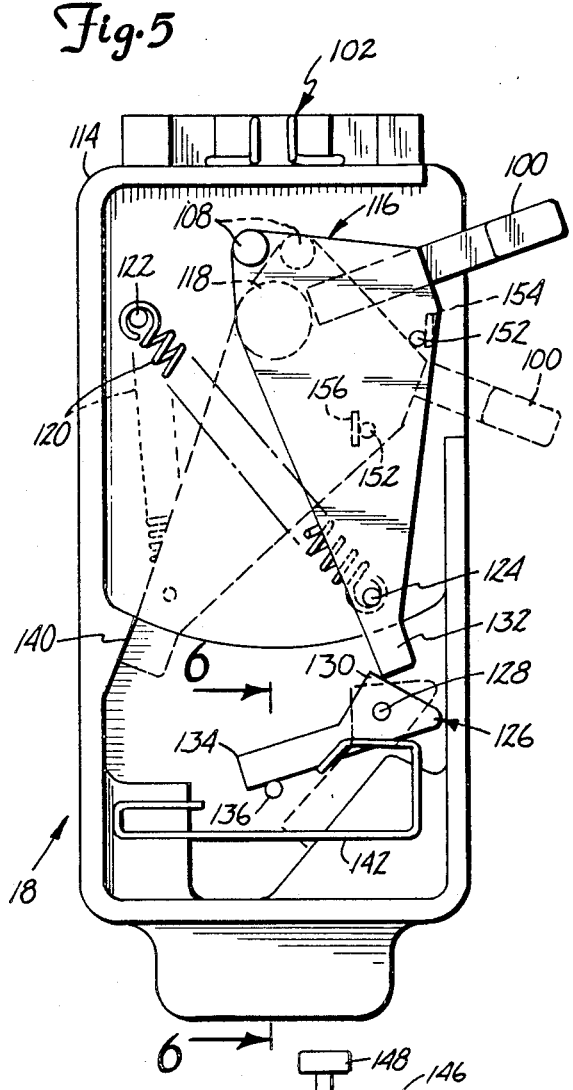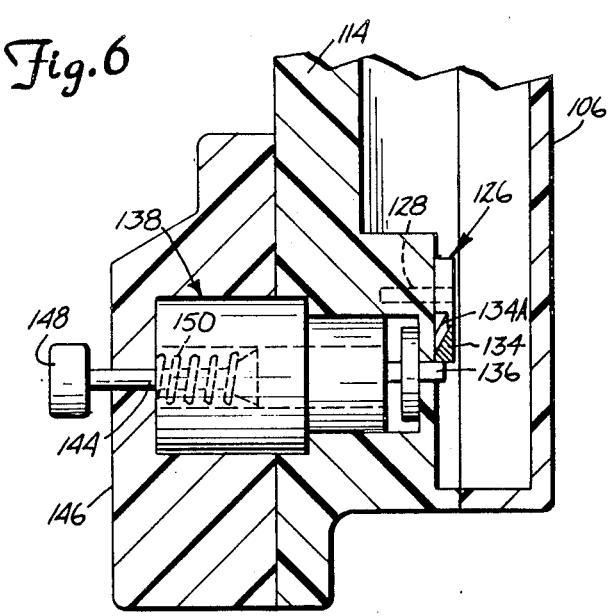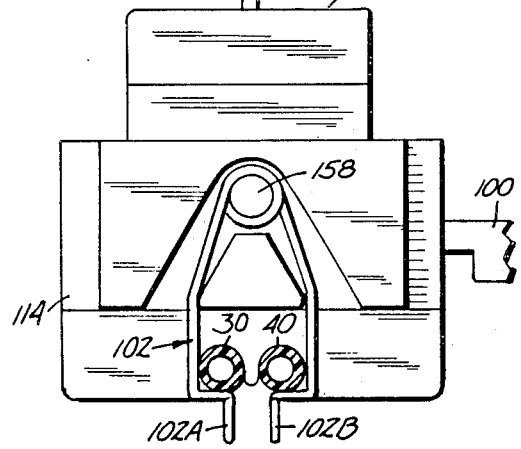

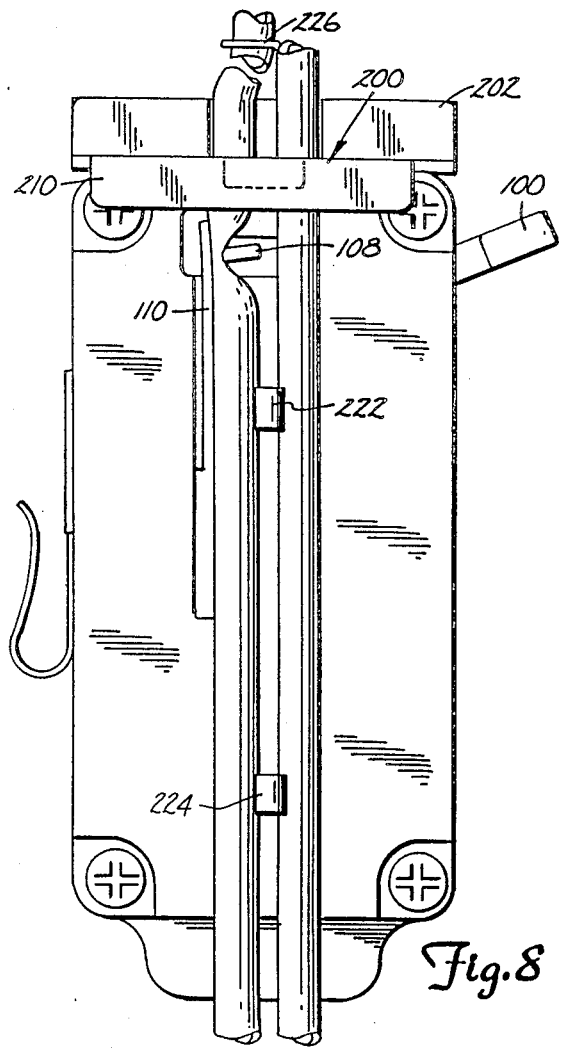
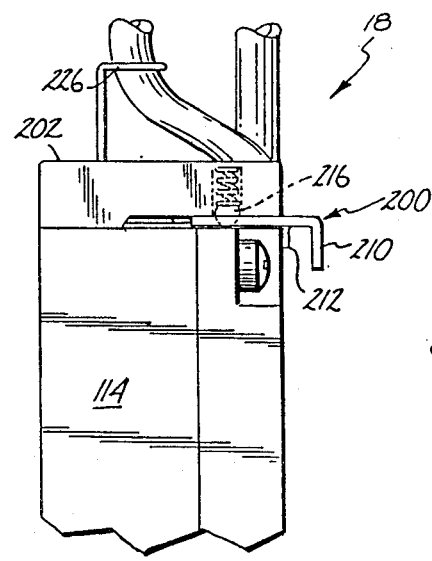

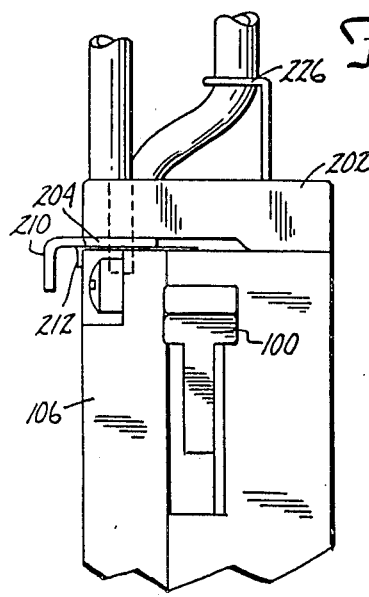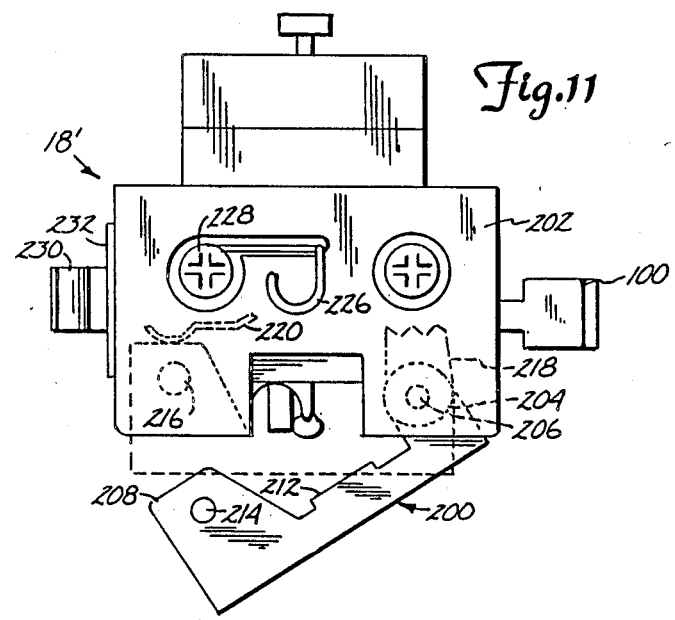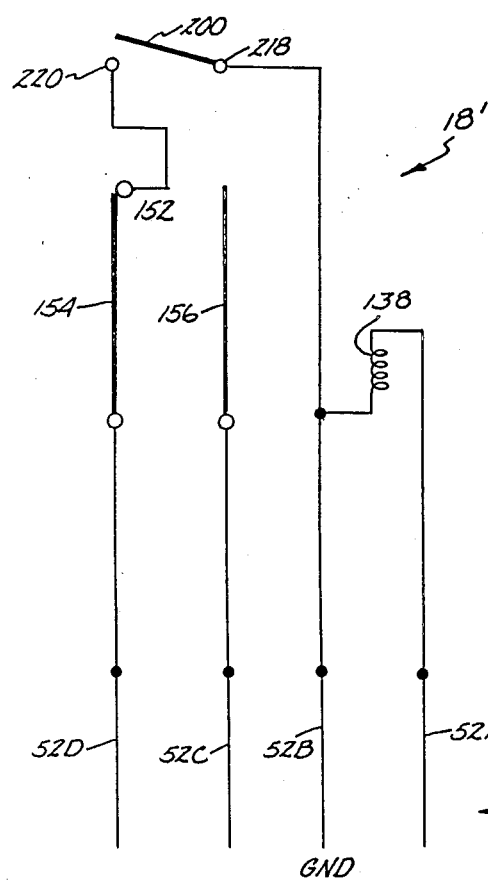

4,673,389

SEQUENCE VALVE FOR PIGGYBACK IV ADMINISTRATION

REFERENCE TO COPENDING APPLICATION

Reference is made to a copending application Ser. No. 676,009 by G. K. Archibald entitled "Multiple Solution IV System" filed on even date with this application and assigned to the same assignee.

BACKGROUND OF THE INVENTION

1. Field of the Invention

The present invention relates to administration of intravenous (IV) fluid. In particular, the present invention is an IV administration system which supplies multiple IV solutions or medications at predetermined intervals to a patient.

2. Description of the Prior Art

It is quite common in IV therapy to give a patient a primary solution and one or more secondary solutions or medications. The secondary (or "piggyback") medication is usually given several times a day. An example is when a patient is on antibiotics. It is desirable to have an IV pump and a sequencing valve that administers the primary and secondary solutions sequentially.

In the past, there have been IV pump systems which allow two fluids to be administered. In these systems, the secondary medication is pumped until the secondary container goes empty, and then the pump switches to the primary fluid. An example of this type of system is shown in U.S. Pat. No. 4,451,255. This proves to be a substantial burden to hospital personnel particularly where the secondary medication is required several times a day. With the prior art systems, the medical personnel must change secondary medication bags several times each day.

SUMMARY OF THE INVENTION

The present invention is an improved IV administration system which has a sequence valve which operates on two tubes which are connected between the inlet of an IV control device (e.g. a pump or controller) and a pair of sources of IV fluids. The sequence valve is set to a first state in which the first tube is pinched off and the second is open. In response to a valve control signal, the sequence valve changes to a second state in which the second tube is pinched off and the first tube is open.

The sequence valve preferably includes a base, a crank pivotally connected to the base, bias means for applying a bias force to the crank, occluder means connected to the crank, and releasable latch means for latching the crank in a first crank position. When the crank is in the first crank position, the occluder means occludes the first tube, and when the crank is in the second crank position, the occluder means occludes the second tube.

The bias force urges the crank toward the second crank position, but when the crank is in the first crank position it is held there by the releasable latch means. In response to a control signal, the releasable latch means releases the crank, thus allowing the crank to move to the second crank position and allowing the sequence valve to switch from the first state to the second state.

BRIEF DESCRIPTION OF THE DRAWINGS

FIG. 4 is a front view of a first preferred embodiment of the sequence valve.

FIG. 5 is a front view of the sequence valve of FIG. 4 with the front cover removed.

FIG. 6 is a sectional view along section 6—6 of FIG. 5.

FIG. 7 is a top view of the valve of FIG. 4.

FIG. 8 is a front view of a second preferred embodiment of the sequence valve.

FIGS. 9 and 10 are partial left and right side views of the sequence valve of FIG. 8.

FIG. 11 is a top view of the sequence valve of FIG. 8 with the tube retainer pivoted to its open position.

FIG. 12 is an electrical schematic diagram of the sequence valve of FIG. 8.

DETAILED DESCRIPTION OF THE PREFERRED EMBODIMENTS

Figure 1:
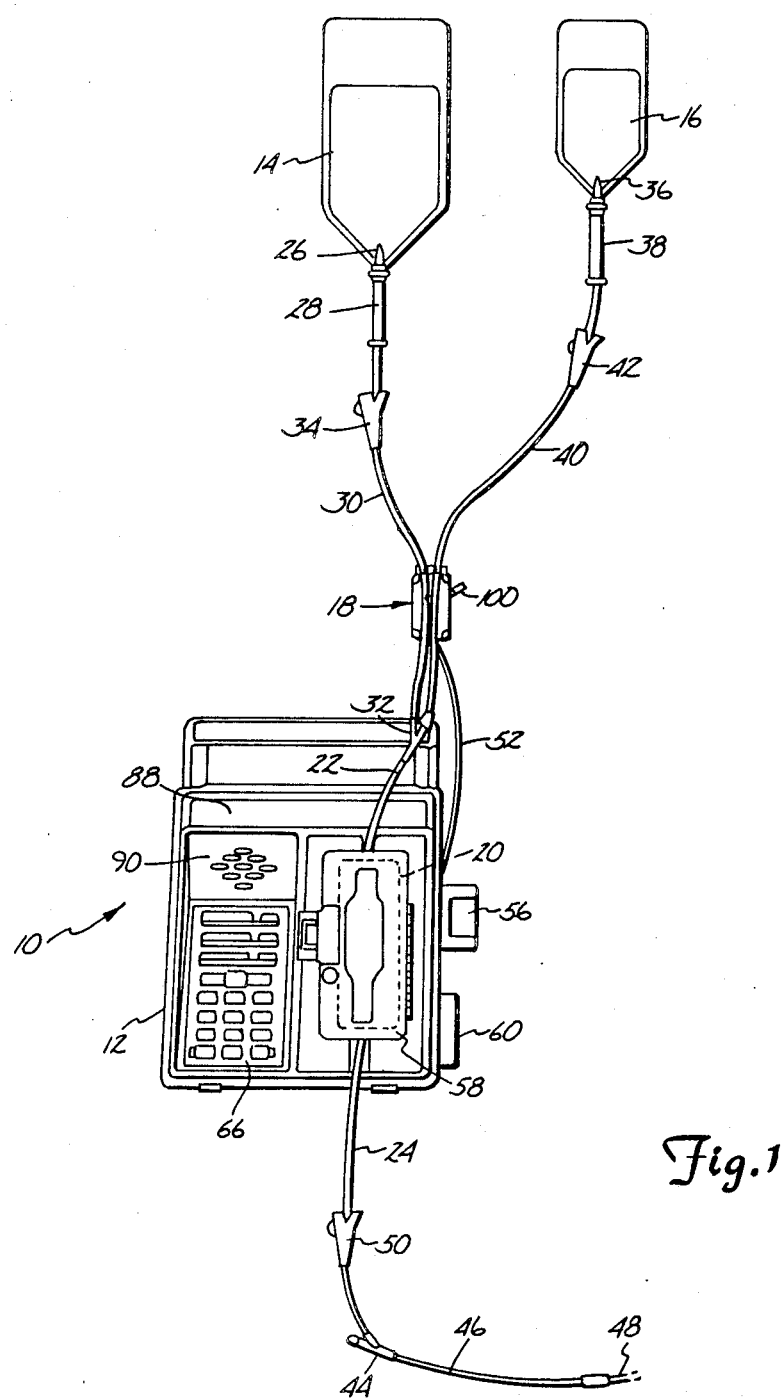
FIG. 1 is a partially schematic diagram of a preferred embodiment of the IV administration system using the sequence valve of the present invention.

In the preferred embodiment shown in FIG. 1, IV administration system 10 includes IV pump 12, which pumps fluid from primary solution bag 14 or secondary (or piggyback) solution bag 16, to a patient (not shown). Sequence valve 18 is connected between bags 14 and 16 and pump 12 to select one of the bags 14 and 16 for connection to pump 12.

In the particular embodiment shown in FIG. 1, pump 12 is an IV pump such as the AVI GUARDIAN 400 pump manufactured by applicant's assignee AVI, inc. Pumps of this general type (which are described in U.S. Pat. No. 4,236,880) use a disposable multiple rolling diaphragm pumping chamber 20 which is inserted into pump 12. Pumping chamber 20 has an inlet tubing 22 connected at its inlet end, and an outlet tubing 24 at its outlet end. A drive mechanism within pump 12 causes relative movement of two of the rolling diaphragms of pumping chamber 20 and the operation of two valves to cause fluid to be pumped from inlet tubing 22 through pumping chamber 20 and out through outlet tubing 24 to the patient.

In the embodiment shown in FIG. 1, disposable multiple rolling diaphragm pumping chamber 20, inlet tubing 22 and outlet tubing 24 form a part of a disposable IV administration set which also includes primary spike 26, primary drip chamber 28, primary tubing 30, proximal Y connector 32, primary roller clamp 34, secondary spike 36, secondary drip chamber 38, secondary tubing 40, secondary roller clamp 42, distal Y connector 44, distal tubing 46, needle 48, and distal roller clamp 50.

Primary spike 26 is inserted into the lower end of primary bag 14, and is connected to the upper end of primary drip chamber 28. The lower end of primary drip chamber 28 is connected by primary tubing 30 to one leg of proximal Y connector 32.

Similarly, secondary spike 36 is inserted into the lower end of secondary bag 16 and is connected to the upper end of secondary drip chamber 38. The lower end of secondary drip chamber 38 is connected through secondary tubing 40 to the second leg of proximal Y connector 32. The third leg of Y connector 32 is connected to inlet tubing 22.

Primary tubing 30 and secondary tubing 40 pass through sequence valve 18, and at least one (preferably primary tubing 30) supports sequence valve 18. In the preferred embodiment of the present invention, sequence valve 18 is a light-weight, solenoid actuated device which initially pinches off primary tubing 30 to prevent flow from primary bag 14 while permitting flow from secondary bag 16 to pumping chamber 20. In response to a valve control signal received from pump 12 through multiconductor cable 52, sequence valve 18 switches so that secondary tubing 40 is pinched off and primary tubing 30 is unobstructed. When secondary tubing 40 is unobstructed and primary tubing 30 is pinched off, secondary (piggyback) bag 16 is connected to inlet tubing 22, and pump 12 pumps the secondary medication from piggyback bag 16 to the patient. Conversely, when secondary tubing 40 is pinched off and primary tubing 30 is unobstructed, the primary solution is pumped from primary bag 14 to the patient by IV pump 12.

At the outlet end, outlet tubing 24 is connected through distal Y connector 44 to distal tubing 46. At the end of distal tubing 46 is needle 48, which is inserted into a vein of the patient. Distal Y connector 44 has another leg which is normally closed, but which allows the insertion of a syringe needle to introduce medication directly into distal tubing 46 as fluid is being pumped to the patient.

Roller clamps 34, 42 and 50 are used by medical personnel during the installation of the IV administration set into pump 12, during initial set-up, and during removal of the IV administration set.

Figure 2:
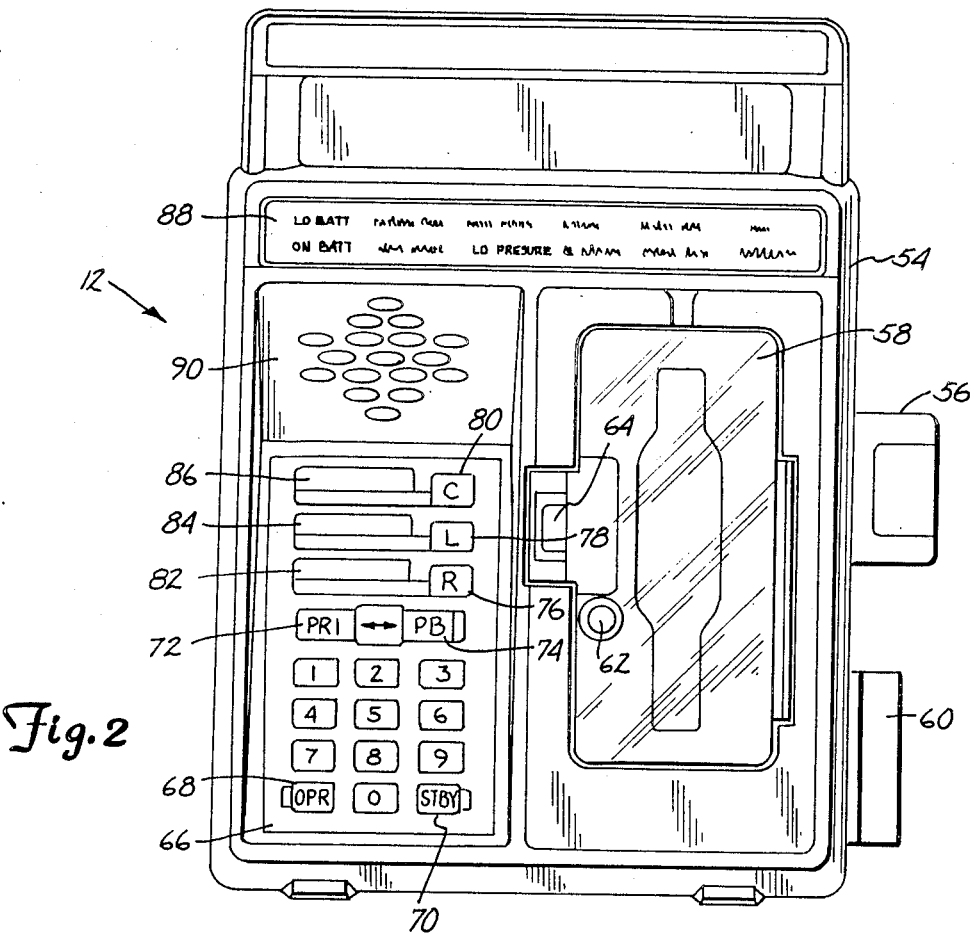
FIG. 2 is a front view of the IV pump of FIG. 1.

FIG. 2 shows a front view of pump 12. Pump 12 includes a housing 54 which contains the electrical control circuitry and the mechanical portions of the pump which interact with disposable pumping chamber 20. Pump 12 is supported on an IV stand or pole (not shown) by pole clamp 56. Door 58 covers a receptacle into which disposable pumping chamber 20 is inserted. In the embodiment shown in FIG. 2, the opening of door 58 requires operation of the three separate devices: load control handle 60, door lock 62, and door latch 64. During normal operation, when the IV administration set is installed with pumping chamber 20 within the receptacle of pump 12, door 58 is closed as shown in FIG. 2.

In the lower left corner of the front of pump 12 is control panel 66, which includes a keyboard formed by numerical key pads ("0" through "9"), operate key pad (OPR) 68, standby key pad (STBY) 70, PRIMARY key pad 72, PIGGYBACK key pad 74, RATE key pad 76, volume limit (LIMIT) key pad 78, and volume infused clear (CLEAR) key pad 80. Control panel 66 also includes three digital displays: rate display 82, volume limit display 84, and volume infused display 86.

Pump 12 also includes indicator panel 88, (which provides visual indication of different error or alarm conditions), and audio alarm annunciator 90.

Figure 3:
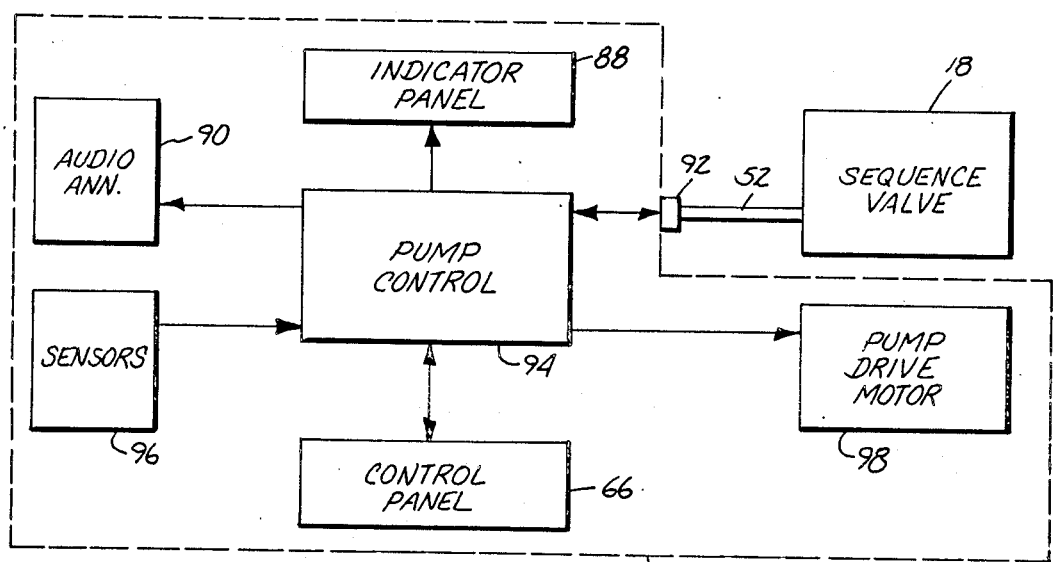
FIG. 3 is an electrical block diagram of the system of FIG. 1.

FIG. 3 is an electrical block diagram of pump 12 and sequence valve 18, which are connected together by multiconductor cable 52 and connector 92 Sequence valve 18 receives a valve control signal from pump 12, and provides a valve state signal, which indicates which fluid line (primary tubing 30 or secondary tubing 40) is occluded.

The operation of pump 12 is controlled by pump control 94, which in preferred embodiments includes a microcomputer, together with associated memory, timing and clock circuitry and appropriate interface circuitry. Pump control 94 receives input signals from control panel 66, from sensors 96 (which sense various operating conditions or parameters such as output pressure, air bubbles in the IV administration set, empty bags and opening of door 58), and from sequence valve 18. Pump control 94 provides outputs to displays 82, 84 and 86 of control panel 66, indicator panel 88, audio annunciator 90 and to pump drive motor 98. In addition, when sequence valve 18 is connected to pump 12 and a piggyback operation has been selected, pump control 94 provides the valve control signal to sequence valve 18.

Control panel 66 allows the medical personnel to "set up" an IV administration schedule so that predetermined volumes of the primary and secondary solutions are delivered at predetermined rates. Pump control 94 controls the operation of both sequence valve 18 and pump drive motor 98, so that it controls both the particular solution being pumped at any given time, and the rate at which the fluid is being pumped.

By depressing STBY key pad 70, the medical personnel places pump 12 in a standby mode. This allows changing or resetting of both rates and volume limits for both the primary and piggyback solutions. The primary solution rate is selected by depressing PRIMARY key pad 72 and then RATE key pad 76, followed by the keys representing the numerical value desired. The primary volume limits can then be set by pressing LIMIT key pad 78 and then using the numerical keys to enter the desired numerical limit for the primary solution.

For the piggyback or secondary solution, PIGGYBACK key pad 74 is pressed. RATE key pad 76 is then pressed, followed by appropriate numerical keys to enter the piggyback rate. LIMIT key pad 78 is then depressed, followed by selected numerical key pads to set the piggyback volume limit.

Pump control 94 stores the rates and volume limits entered for both the primary solution and the piggyback solution. These stored values are used, together with an accumulated volume infused value in controlling sequence valve 18 as well as pump drive motor 98.

Sequence valve 18 of the present invention is a spring loaded, solenoid actuated device which initially occludes primary tubing 30 so that the secondary solution is pumped first. Sequence valve 18 is placed in this initial condition by inserting primary tubing 30 into one slot of sequence valve 18 and then cocking lever 100 so that primary tubing 30 is occluded. Secondary tubing 40 is then inserted into an adjacent slot alongside primary tubing 30 in sequence valve 18 as shown in FIG. 1.

Operation of pump 12 in the piggyback mode is initiated by depressing OPR key pad 18. Pump control 94 provides pump drive control signals to pump drive motor 98 which cause motor 98 to produce the pumping rate stored for the piggyback solution. As pump drive motor 98 is operated, pump control 94 maintains an accumulated value which represents the amount of secondary solution which has been pumped with sequence valve 18 in its initial setting. When that accumulated value reaches the piggyback volume limit stored by pump control 94, a valve control signal is produced which causes sequence valve 18 to change state. Sequence valve 18, in response to the valve control signal, occludes secondary tubing 40, and allows primary solution to flow through primary tubing 30, to inlet tubing 22. Upon receiving the signal from sequence valve 18 indicating that the change has been made, pump control 94 provides pump drive signals which cause pump drive motor 98 to operate at the pumping rate selected for the primary solution. Pump control 94 again maintains an accumulated value which represents the amount of primary solution which has been pumped. This value is displayed on volume infused display 86. When the accumulated value reaches the stored primary volume limit, pump control 94 halts operation of pump drive motor 98 and provides an indication through indicator panel 88 and audio annunciator 90 that both the piggyback and primary administration has been completed. At that point, the medical personnel responsible for the IV administration are required to intervene to set a new schedule of primary and piggyback rates and volume rates.

The present invention is advantageous because all of the medication for a single day or for several days can be stored in one large secondary bag 16, as opposed to much smaller secondary bags which run dry after each administration of that medication. For example, if a patient is to receive 50 milliliters of secondary medication four times a day, four bags would be required with the prior art systems, in which the switching from the secondary bag to the primary solution is determined by when the secondary bag is empty. With the system of the present invention, one 200 milliliter bag can be used for the entire day. Since a large or a small bag costs essentially the same, there is a cost saving just by virtue of the reduced number of bags. In addition, the system significantly reduces the amount of time which is required of medical personnel. It is not necessary to change the secondary bag 16 after each administration of medication, and in fact the present invention allows the secondary medication to be provided multiple times without a change in the secondary bag.

By use of pump control 94 within housing 54 of pump 12 to control operation of both pump 12 and sequence valve 18, the size, weight, complexity and cost of sequence valve 18 are significantly reduced. As a result, sequence valve 18 can be suspended from the tubing (e.g. primary tubing 30) rather than requiring separate clamping to a pole. This makes sequence valve 18 simpler and easier to use, and makes it portable so that sequence valve 18 can be moved wherever pump 12 is moved.

FIGS. 4 through 7 show a first preferred embodiment of sequence valve 18. FIG. 4 shows valve 18 in its normal initial operating position for piggyback operation. As shown in FIG. 4, tubes 30 and 40 pass side-by-side through valve 18. At the upper end, tubing 30 and tubing 40 are retained by retainer spring 102, which has a pair of retainer arms 102A and 102B. At the lower end, tubing 30 and tubing 40 are retained in side-by-side position by retaining fingers 104A and 104B of front cover 106.

As shown in FIG. 4, lever 100 is in its uppermost ("cocked") position, which causes occluder stud 108 to be in its leftmost position. As a result, primary tubing 30 is pinched off between occluder stud 108 and leaf spring 110. Also shown in phantom in FIG. 4 is the position of lever 100 and the position of occluder stud 108 after sequence valve 18 has received a valve control signal from pump 12 which causes occluder stud 108 to move generally to the right to pinch off secondary tubing 40 between occluder stud 108 and wall 112. Thus sequence valve 18 has two stable positions, one in which primary tubing 30 is occluded and secondary tubing 40 is unoccluded; and the other in which secondary tubing 40 is occluded and primary tubing 30 is unoccluded.

FIG. 5 shows sequence valve 18 with front cover 106 removed. The operating mechanisms of sequence valve 18 are supported by valve base 114. Both occluder stud 108 and lever 100 are attached to bell crank 116, which is pivotally mounted to valve base 114 by pivot pin 118.

As in FIG. 4, two positions of occluder stud 108 and the other moving parts of sequence valve 18 are shown. Solid lines represent the initial position in which primary tubing 30 is occluded, and phantom lines to illustrate the second position in which secondary tubing 40 is occluded.

Bell crank 116 is biased in a clockwise direction by bias spring 120, which is connected at its upper end to stud 122 and thus to valve base 114, and which is connected at its lower end to stud 124 which projects rearwardly from the lower end of bell crank 118.

Latch 126 is pivotally mounted about pivot pin 128, and has a latch tooth 130 which engages lower leg 132 of bell crank 116 when lever 116 is its cocked upper position. Latch arm 134 is held in the initial position by solenoid plunger 136, which prevents rotation of latch 126 about the axis defined by pivot pin 128.

Valve 18 will remain in a stable initial position until a valve control signal actuates solenoid 138 (FIG. 6). This causes solenoid plunger 136 to be pulled in a rearward direction out of contact with arm 134 of latch 126. This allows the bias force of spring 120 to rotate bell crank 116 and in turn latch 126 about their respective pivot pins 118 and 128 to the position shown in phantom in FIG. 5. The second stable position of bell crank 116 is defined by stop 140, which engages leg 132 of bell crank 116 to prevent further rotation in the clockwise direction. In this second stable state, occluder stud 108 is at its rightmost position, so that secondary tubing 40 is pinched off between occluder stud 108 and wall 112.

Sequence valve 18 is reset to its initial position by moving lever 100 upwards to the initial cocked position shown in solid lines. Latch spring 142 urges latch 126 back to its initial position when sequence valve 18 is being reinitialized. As shown in FIG. 6, rear surface 134A of arm 134 is bevelled to form a ramp which allows arm 134 to move past solenoid plunger 136 as lever 100 is being cocked.

Solenoid 138 includes a solenoid plunger stud 144 which extends out the rear end of solenoid cover 146. At the rear end of solenoid plunger stud 144 is solenoid button 148. This button allows the nurse or technician to pull solenoid plunger 136 out of the way of latch 126 in order to manually release lever 100, bell crank 116 and latch 126 from the cocked position. Button 148 can then be released and, due to the bias force of bias spring 150, solenoid plunger 136 returns to its normal position shown in FIG. 6.

It is also preferable for sequence valve 18 to provide an electrical signal which indicates the current state of sequence valve 18. In the embodiment shown in FIG. 5, a metal contact stud 152 is attached to bell crank 116. When valve 18 is in its initial state, contact stud 152 is in contact with contact wire 154. When the valve control signal has been received and bell crank 116 has rotated to the position shown in phantom, contact stud 152 has moved into engagement with contact wire 156. Depending upon which wire 154 or 156 is in contact with contact stud 152, a different electrical signal is supplied through cable 52 to pump 12. This provides a simple, yet very effective way of indicating the state of sequence valve 18 to pump 12.

As shown in FIG. 7, upper retainer 102 is a single wire clip which mounts over stud 158 at the upper end of valve base 114. The resilient nature of retainer 102 allows the retainer arms 102A and 102B to be displaced outwardly while tubing 30 and 40 are inserted into sequence valve 18. Once released, arms 102A and 102B return to their normal position shown in FIG. 7, thus securely holding tubing 30 and tubing 40 in place.

Sequence valve 18 shown in FIGS. 4-7 is particularly advantageous, since it is small, light-weight (so that it can be supported on tubing 30 and 40 without the need for a separate support stand) and uses a small, low-power solenoid. By using a pivoted latch 126 and a pivoted bell crank 116, both of which provide a substantial mechanical advantage (e.g. 4:0 each), a very small movement of solenoid plunger 136 provides the sufficient force to move occluder stud 108 to the right so as to pinch off tubing 40. The force required to move solenoid plunger 136 is, for example, only one-sixteenth of the force applied by occluder stud 108 to tubing 40.

Sequence valve 18 shown in FIGS. 4-7 also uses an extremely simple mechanism to pinch off alternately either tubing 30 or tubing 40. By the use of leaf spring 110 to urge tubing 30 toward occluder stud 108, sequence valve 18 does not require a precise alignment of both positions of occluder stud 108, and variations in the diameters of tubing 30 and 40 are accommodated. It is merely necessary to ensure that occluder stud 108 moves far enough to the right to pinch off tubing 40 against right wall 112 for the minimum expected diameter of tubing 40.

FIGS. 8-12 show a second embodiment of the sequence valve of the present invention. This second embodiment (which is designated valve 18') is generally similar to the embodiment of sequence valve 18 shown in FIGS. 4-7, and similar reference numerals are used to designate similar elements. The internal operation of the bell crank, latch and solenoid of sequence valve 18' of FIGS. 8-12 are identical to those shown in FIGS. 4-7 and will not be discussed again.

The main difference between sequence valve 18' of FIGS. 8-12 and sequence valve 18 of FIGS. 4-7 is in the retaining of tubing 30 and 40. In sequence valve 18', a tube retainer 200 is pivotally mounted at the upper end of valve 18' between top end plate 202 and the upper ends of front cover 106 and valve base 114. Tube retainer 200 has a right leg 204 which is pivotally mounted about pivot pin 206, a left leg 208, a front flange 210, and a tube hold-down flange 212. The closed position of tube retainer 200 is shown in FIGS. 8-10, and the open position is shown in FIG. 11. Flange 210 forms a handle by which the nurse can pivot tube retainer 200 to the open position to allow insertion or removal of tubing 30 and 40 from sequence valve 18'.

Left leg 208 of tube retainer 200 contains a hole 214 which receives a spring loaded ball 216 mounted in top plate 202 when tube retainer 200 is in the closed position shown in FIGS. 8-10. Spring loaded ball 216 maintains tube retainer 200 in the closed position and prevents it from moving from the closed position if IV pump 12 or tubing 30 or 40 are moved or bumped inadvertently.

Sequence valve 18 also uses tube retainer 200 as a switch to indicate to pump 12 that sequence valve 18' is in a condition to operate. For this purpose, tube retainer 200 is an electrically conductive material, preferably metal. An electrically conductive washer 218, which is partially shown in FIG. 11, is mounted on pivot pin 206 in contact with right leg 204 of tube retainer 200. Spring Contact 220 is positioned so that it will be engaged by left leg 208 when tube retainer 200 is in the closed position. Thus when tube retainer 200 is in the closed position, a closed electrical path is provided between conductive washer 218 and spring contact 220.

FIG. 12 shows an electrical schematic diagram of sequence valve 18'. In this embodiment, cable 52 (which connects valve 18' to pump control 94) contains four wires 52A-52D. Solenoid 138 is connected between wires 52A and 52B. Wire 52B is connected to ground. When pump control 94 causes a voltage to be present between wires 52A and 52B, solenoid 138 is actuated.

Wires 52C and 52D are used to indicate to pump control 94 the condition or state of sequence valve 18'. The switch formed by tube retainer 200, conductive washer 218 and spring contact 220 is connected in series with a switch formed by contact stud 152 and contact wires 154 and 156. Contact wire 154 is connected to wire 52D, and contact wire 156 is connected to wire 52C.

If tube retainer 200 is in its open position, both wires 52C and 52D will indicate an open circuit. When tube retainer 200 is closed, normally one of the two wires 52C and 52D will be an open circuit, while the other will be connected to ground. By monitoring wires 52C and 52D, therefore, pump control 94 can determine the operating state of sequence valve 18', as well as whether tube retainer 200 is in closed position.

FIGS. 8-11 also show retainer posts 222 and 224, which are positioned along the channel, and which maintain tubing 30 and 40 in position along the entire length of the channel.

At the upper end of valve 18' is hook 226, which is attached by screw 228 to top plate 202. Primary tubing 30 is threaded through hook 226 to maintain sequence valve 18' in a generally vertical position. This counteracts the tendency of the lower end of valve 18' to tip forward due to the greater weight of solenoid 138 within solenoid housing 146 (see FIG. 6).

Also included in sequence valve 18' is a spring clip 230 and retainer pad 232 which are positioned along the left side of sequence valve 18'. Clip 230 allows sequence valve 18' to be clipped onto pump 12 when not in use. Pad 232 prevents sequence valve 18' from slipping when it is clipped onto pump 12.

Although the present invention has been described with reference to preferred embodiments, workers skilled in the art will recognize that changes may be made in form and detail without departing from the spirit and scope of the invention. For example, although the present invention has been described in the context of a system in which a primary and only one secondary bag are used, it is also applicable to more complex systems in which multiple secondary bags are used in conjunction with a primary bag.

Similarly, although the present invention has been described in the context of a specific type of IV pump sold by applicant's assignee, the present invention is applicable to other IV pump and controller systems as well.

What is claimed is:

1. A sequence valve having a first state in which a first flexible tube is occluded and a second flexible tube is not and a second state in which the second tube is occluded and the first tube is not, the sequence valve being manually settable to the first state and switching to the second state in response to a control signal, the sequence valve comprising:

a base;

a crank pivotally connected to the base for movement between first and second crank positions, in which the sequence valve has the first state when the crank is in the first crank position and has the second state when the crank is in the second crank position;

bias means for providing a bias force to the crank which urges the crank toward the second crank position;

occluder means connected to a first end of the crank for occluding the first flexible tube when the crank is in the first crank position, and for occluding the second flexible tube when the crank is in the second crank position;

manually movable means connected to the crank for moving the crank to the first crank position;

a latch pivotally connected to the base, the latch having an arm and having a latch tooth for engaging a second end of the crank when the crank is moved to the first crank position by the manually movable means; and a solenoid having a plunger which engages the arm of the latch to hold the latch tooth in engagement with the second end of the crank when the crank is in the first crank position, the solenoid being responsive to the control signal to move the plunger out of engagement with the arm to allow rotation of the latch and thereby allow the bias force to rotate the crank from the first crank position to the second crank position, wherein the solenoid is normally deenergized when the sequence valve is in the first state and when the sequence valve is in the second state, and is energized by the control signal to cause a transition from the first to the second state.

2. The sequence valve of claim 1 and further comprising:

a latch spring for urging the latch toward a position in which the latch tooth engages the second end of the crank.

3. The sequence valve of claim 1 wherein the crank is pivotally connected to the base at a pivot point located between the occluder means and the second end of the crank.

4. The sequence valve of claim 3 wherein the pivot point is positioned closer to the first end than to the second end of the crank.

5. The sequence valve of claim 1 wherein the manually movable means comprises:

a lever connected to the crank for moving the crank to the first crank position.

6. The sequence valve of claim 1 and further comprising:

contact means for contacting a first switch element when the crank is in the first crank position and for contacting a second switch element when the crank is in the second crank position to provide signals representative of the position of the crank.

7. The sequence valve of claim 1 and further comprising:

a channel for positioning the first and second tubes in side-by-side relationship.

8. The sequence valve of claim 7 and further comprising:

tube retaining means for holding the first and second tubes in position in the channel.

9. The sequence valve of claim 8 wherein the tube retaining means comprises a tube retainer positioned at a first end of the channel and pivotable between an open position in which tubes can be inserted into or removed from the channel and a closed position which holds the tubes in the channel.

10. The sequence valve of claim 9 and further comprising:

means for providing a signal which indicates whether the tube retainer is in its closed position.

11. The sequence valve of claim 7 wherein the occluder means comprises an occluder stud connected to the crank and extending into the channel between the first and second tubes so that when the crank is in the first crank position the occluder stud causes the first tube to be pinched off and when the crank is in the second crank position the occluder stud causes the second tube to be pinched off.

12. The sequence valve of claim 11 and further comprising:

a leaf spring on one side of the channel for urging the first tube toward the occluder stud and means positioned on the other side of the channel for engaging the second tube.

13. A sequence valve having a first state in which a first flexible tube is occluded and a second flexible tube is not and a second state in which the second tube is occluded and the first tube is not, the sequence valve being manually settable to the first state and switching to the second state in response to a control signal, the sequence valve comprising:

a base;

a pivotable tube pincher connected to the base, having means for pinching off the first tube when the valve is in the first state and the tube pincher is in a first position and then the second flexible tube when the valve is in the second state and the tube pincher is in a second position;

bias means for applying a bias force to the tube pincher in a direction toward the second position;

manually movable means connected to the tube pincher for moving the tube pincher against the bias force to the first position in which the first tube in pinched off;

pivotable latch means for engaging and holding the tube pincher in the first position in which the first tube is pinched off, wherein the latch has a latch tooth and an arm, the latch having a first latch position in which the latch tooth holds the tube pincher and having a second latch position in which the latch tooth is out of engagement with the tube pincher; and solenoid means which releases the latch in response to the control signal to permit the latch to pivot out of engagement with the tube pincher and thereby allow the bias force to pivot the tube pincher to a position in which the second tube is pinched off, wherein the solenoid has a plunger for engaging the arm of the latch in the first latch position to hold the latch and for moving out of engagement with the arm in response to the control signal to release the latch, wherein the solenoid is normally deenergized when the sequence valve is in the first state and when the sequence valve is in the second state, and is energized by the control signal to cause a transition from the first to the second state.

14. The sequence valve of claim 13 and further comprising:
   contact means for contacting a first switch element when the tube pincher is in the first position in which the first tube is pinched off and for contacting a second switch element when the tube pincher is in the second position in which the second tube is pinched off to provide signals representative of the position of the tube pincher.

15. The sequence valve of claim 13 wherein the tube pincher comprises:
   a pivotable crank; and
   an occluder stud connected to the crank for pinching off one of the first and second tubes depending upon the position of the crank; and
   wherein the bias means comprises a bias spring for applying the bias force to the crank.

16. The sequence valve of claim 15 and further comprising a channel in which the tubes are positioned in side-by-side relationship and wherein the occluder stud extends into the channel between the first and second tubes and is movable in a generally transverse direction as the crank moves.

17. The sequence valve of claim 16 and further comprising:
   tube retaining means positioned at a first end of the channel for holding the first and second tubes in position in the channel.

18. An IV administraion system comprising:
   a first source of a first IV fluid;
   a second source of a second IV fluid;
   an IV control device having an inlet and an outlet for delivering IV fluids;
   a first flexible tube connected between the first source and the inlet;
   a second flexible tube connected between the second source and the inlet;
   a sequence valve having a first state in which a first flexible tube is occluded and a second flexible tube is not and a second state in which the second tube is occluded and the first tube is not, the sequence valve being manually settable to the first state and switching to the second state in response to a control signal, valve comprising:
   a base;
   a crank pivotally connected to the base for movement between first and second crank positions;
   bias means for providing a bias force to the crank which urges the crank toward the second crank position;
   occluder means connected to a first end of the crank for occluding the first flexible tube when the crank is in the first crank position, and for occluding the second flexible tube when the crank is in the second crank position;
   manually movable means connected to the crank for moving the crank to the first crank position;
   a latch pivotally connected to the base, the latch having an arm and having a latch tooth for engaging a second end of the crank when the crank is moved to the first crank position by the manually movable means;
   a solenoid having a plunger which engages the arm of the latch to hold the latch tooth in engagement with the second end of the crank when the crank is in the first crank position, the solenoid being responsive to the control signal to move the plunger out of engagement with the arm to allow rotation of the latch and thereby allow the bias force to rotate the crank from the first crank position to the second crank position, wherein the solenoid is normally deenergized when the sequence valve is in the first state and when the sequence valve is in the second state, and is energized by the control signal to cause a transition from the first to the second state; and
   means for providing the control signal to the sequence valve.

19. The system of claim 18 wherein the sequence valve further comprises:
   a latch for urging the latch toward a position in which the latch tooth engages the second end of the crank.

20. The system of claim 18 wherein the crank is pivotally connected to the base at a pivot point located between the occluder means and the second end of the crank.

21. The system of claim 20 wherein the pivot point is positioned closer to the first end than to the second end of the crank.

22. The system of claim 18 wherein the manually movable means comprises:
   a lever connected to the crank for moving the crank to the first crank position.

23. The system of claim 18 wherein the sequence valve further comprises:
   contact means for contacting a first switch element when the crank is in the first crank position and for contacting a second switch element when the crank is in the second crank position to provide signals representative of the position of the crank.

24. The system of claim 18 wherein the sequence valve further comprises:
   a channel for positioning the first and second tubes in side-by-side relationship.

25. The system of claim 24 wherein the sequence valve comprises:
   tube retaining means positioned at a first end of the channel for holding the first and second tubes in position in the channel.

26. The sequence valve of claim 25 wherein the tube retaining means comprises a tube retainer positioned at a first end of the channel and pivotable between an open position in which tubes can be inserted into or removed from the channel and a closed position which holds the tubes in the channel.

27. The sequence valve of claim 26 and further comprising:
   means for providing a signal which indicates whether the tube retainer is in its closed position.

28. The system of claim 24 wherein the occluder means comprises an occluder stud connected to the crank and extending into the channel between the first and second tubes so that when the crank is in the first crank position the occluder stud causes the first tube to be pinched off and when the crank is in the second crank position the occluder stud causes the second tube to be pinched off.

29. An IV administration system comprising:
   a first source of a first IV fluid;
   a second source of a second IV fluid;
   an IV control device having an inlet and an outlet for delivering IV fluids;
   a first flexible tube connected between the first source and the inlet;

a second flexible tube connected between the second source and the inlet;

a sequence valve having a first state in which a first flexible tube is occluded and a second flexible tube is not and a second state in which the second tube is occluded and the first tube is not, the sequence valve being manually settable to the first state and switching to the second state in response to a control signal, the sequence valve comprising:

a base;

a pivotable tube-pincher connected to the base, having means for pinching off the first tube when the valve is in the first state and the tube pincher is in a first position and then the second tube when the valve is in the second state and the tube pincher is in a second position;

bias means for applying a bias force to the tube pincher in a direction toward the second position;

manually movable means connected to the tube pincher for moving the tube pincher against the bias force to the first position in which the first tube in pinched off;

pivotable latch means for engaging and holding the tube pincher in the first position in which the first tube is pinched off, wherein the latch has a latch tooth and an arm, the latch having a first latch position in which the latch tooth holds the tube pincher and having a second latch position in which the latch tooth is out of engagement with the tube pincher; and solenoid means which releases the latch in response to the control signal to permit the latch to pivot out of engagement with the tube pincher and thereby allow the bias force to pivot the tube pincher to a position in which the second tube is pinched off, wherein the solenoid has a plunger for engaging the arm of the latch in the first latch position to hold the latch and for moving out of engagement with the arm in response to the control signal to release the latch; and means for providing the control signal to the sequence valve.

* * * * *

UNITED STATES PATENT AND TRADEMARK OFFICE
CERTIFICATE OF CORRECTION

PATENT NO. : 4,673,389

DATED : June 16, 1987

INVENTOR(S) : G. Kent Archibald et al.

It is certified that error appears in the above-identified patent and that said Letters Patent is hereby corrected as shown below:

Column 10, line 24, after "stud", insert --;--.

Column 11, line 29, delete "administraion" and insert --administration--.

Column 12, line 13, after "latch", insert --spring--.

Signed and Sealed this

Twenty-seventh Day of October, 1987

Attest:

DONALD J. QUIGG

*Attesting Officer*　　　*Commissioner of Patents and Trademarks*